(12) United States Patent
Dabrowski

(10) Patent No.: US 8,533,892 B2
(45) Date of Patent: Sep. 17, 2013

(54) SYSTEM FOR SELECTING MODES OF OPERATION IN A POWER TOOTHBRUSH

(75) Inventor: Christopher J. Dabrowski, Lynnwood, WA (US)

(73) Assignee: Koninklijke Philips N.V., Eindhoven (NL)

( * ) Notice: Subject to any disclaimer, the term of this patent is extended or adjusted under 35 U.S.C. 154(b) by 1102 days.

(21) Appl. No.: 12/158,765

(22) PCT Filed: Dec. 19, 2006

(86) PCT No.: PCT/IB2006/054957
§ 371 (c)(1),
(2), (4) Date: Jun. 23, 2008

(87) PCT Pub. No.: WO2007/072430
PCT Pub. Date: Jun. 28, 2007

(65) Prior Publication Data
US 2008/0313829 A1 Dec. 25, 2008

Related U.S. Application Data

(60) Provisional application No. 60/752,653, filed on Dec. 21, 2005.

(51) Int. Cl.
*A46B 9/04* (2006.01)
(52) U.S. Cl.
USPC .......................................... 15/167.1; 15/22.1
(58) Field of Classification Search
USPC ................ 15/22.1, 4, 167.1, 22.2, 22.3, 22.4, 15/23, 24, 25, 26, 27, 28, 29
See application file for complete search history.

(56) References Cited

U.S. PATENT DOCUMENTS

| | | | |
|---|---|---|---|
| 3,489,936 A * | 1/1970 | Boyles | 310/47 |
| 3,771,186 A * | 11/1973 | Moret et al. | 15/22.1 |
| 3,809,977 A * | 5/1974 | Balamuth et al. | 318/116 |
| 4,326,314 A | 4/1982 | Moret | |
| 5,504,959 A * | 4/1996 | Yukawa et al. | 15/22.1 |
| 5,544,382 A * | 8/1996 | Giuliani et al. | 15/22.1 |
| 5,561,881 A * | 10/1996 | Klinger et al. | 15/22.1 |
| 5,784,742 A * | 7/1998 | Giuliani et al. | 15/22.1 |
| 5,864,288 A * | 1/1999 | Hogan | 340/568.1 |
| 5,943,723 A * | 8/1999 | Hilfinger et al. | 15/22.1 |
| 6,611,780 B2 * | 8/2003 | Lundell et al. | 702/122 |
| 6,760,945 B2 * | 7/2004 | Ferber et al. | 15/22.2 |
| 6,836,918 B1 * | 1/2005 | Wong | 15/22.1 |

(Continued)

FOREIGN PATENT DOCUMENTS

| | | |
|---|---|---|
| CH | 475738 | 9/1969 |
| JP | 5137616 A | 6/1993 |

(Continued)

*Primary Examiner* — Lee D Wilson
*Assistant Examiner* — Joel Crandall

(57) ABSTRACT

The mode selection system for a power toothbrush includes a first switch (25) operable to control the ON/OFF condition of the toothbrush and a second switch (29) operable when the first switch is in the OFF condition to select one of a plurality of possible modes of operation programmed in the toothbrush. A pre-established time is set during which the ON/OFF switch must be operated to an ON condition after the mode selection switch has been operated to select a particular mode. The selected mode is indicated by a lit LED on a handle portion of the toothbrush.

11 Claims, 2 Drawing Sheets

(56) References Cited

U.S. PATENT DOCUMENTS

| | | | |
|---|---|---|---|
| 6,883,199 B1 * | 4/2005 | Lundell et al. | 15/22.1 |
| 6,889,829 B2 | 5/2005 | Lev | |
| 6,918,153 B2 * | 7/2005 | Gruber | 15/22.1 |
| 6,954,961 B2 | 10/2005 | Ferber | |
| 6,955,539 B2 * | 10/2005 | Shortt et al. | 433/118 |
| 7,291,940 B2 * | 11/2007 | Bruwer | 307/140 |
| 7,596,827 B1 * | 10/2009 | Puneet | 15/22.1 |
| 7,682,153 B2 * | 3/2010 | Hilfinger et al. | 433/216 |
| 7,748,069 B2 * | 7/2010 | Dawley | 15/22.1 |
| 7,770,251 B2 * | 8/2010 | Hilscher et al. | 15/22.1 |
| 8,046,861 B2 * | 11/2011 | Joseph | 15/22.1 |
| 8,075,315 B2 * | 12/2011 | Gatzemeyer et al. | 434/238 |
| 2002/0092104 A1 | 7/2002 | Ferber | |
| 2002/0133308 A1 | 9/2002 | Lundell | |
| 2003/0017874 A1 * | 1/2003 | Jianfei et al. | 463/46 |
| 2003/0115694 A1 * | 6/2003 | Pace | 15/22.1 |
| 2005/0271531 A1 * | 12/2005 | Brown et al. | 417/474 |
| 2005/0278882 A1 * | 12/2005 | Drzewiecki et al. | 15/105 |
| 2007/0074359 A1 * | 4/2007 | O'Lynn | 15/105 |
| 2008/0313829 A1 * | 12/2008 | Dabrowski | 15/22.1 |

FOREIGN PATENT DOCUMENTS

| | | |
|---|---|---|
| JP | 9173149 A | 7/1997 |
| JP | 2003501137 A | 1/2003 |
| JP | 2005245782 A1 | 6/2008 |

* cited by examiner

SYSTEM FOR SELECTING MODES OF OPERATION IN A POWER TOOTHBRUSH

This invention relates generally to control of the operation of a power toothbrush, and more specifically concerns the selection of operational modes or functions of the power toothbrush by the user.

It is desirable to be able to vary the modes of operation of a power toothbrush in order to provide both a more individual and overall more effective cleaning. For instance, the toothbrush can be operated in various vibrational modes, such as normal, soft and massage and, in addition, modes can be combined in predetermined ways to produce a particular toothbrush operational cycle, again for the purpose of providing more effective brushing, geared precisely to the individual user.

Such operational flexibility requires a user interface, typically on the handle of the toothbrush, for the user to select the desired mode. For a plurality of modes/features, however, and particularly as more features are added to a particular toothbrush, the interface can become cumbersome, create confusion, or be too sophisticated for the average user. Hence, it is desirable to provide the user with an interface which is as simple to use as possible.

Some toothbrushes provide a mode button for selection of various modes, in addition to an ON/OFF button. However, these devices typically have disadvantages, since when the device is operating in the mouth, and the user wishes to select a mode other than a default mode, there is no possibility of visual feedback to ensure that the desired mode has actually been selected. Further, it is often difficult to readily access the mode button when the toothbrush is operating in the mouth. If the mode button is operated on these known toothbrushes to select a desired mode when the toothbrush is operating out of the mouth, splattering of the toothpaste or liquid present on the toothbrush will result, which is also undesirable.

Hence, it would be desirable to have an interface arrangement by which the user can select a desired operating mode, while receiving visual feedback to confirm selection of the desired mode, without the toothbrush being in operation.

Accordingly, the present invention is a system for selection of operation of a power toothbrush, comprising: a toothbrush assembly having a first switch operable by the user to control the ON/OFF condition of the toothbrush, and a second switch, operable by a user during the time that the first switch is in an OFF condition, to select one of a plurality of possible modes of operation established in the toothbrush, wherein when the second switch is operated to select a particular mode of operation, the toothbrush will then operate in that particular mode when the ON/OFF switch is thereafter operated to an ON condition; and an indicator means for indicating which mode has been selected.

Figure 1:
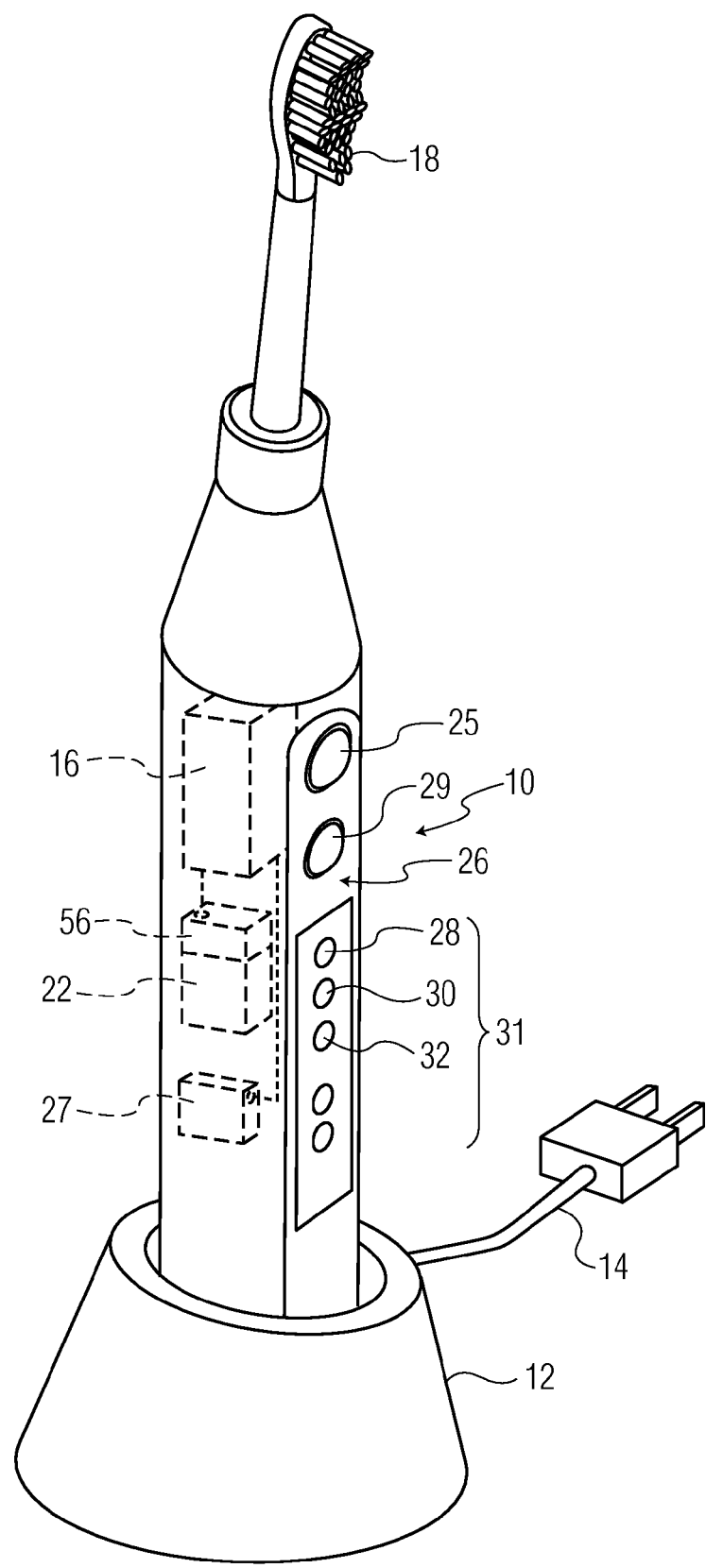
FIG. 1 is a schematic view of a toothbrush with the mode selection arrangement (user interface assembly) of the present invention.

A power toothbrush incorporating the user interface control assembly of the present invention is shown generally at 10. The power toothbrush 10, when not in use, rests in a charger mechanism 12 which is connected to a power outlet by means of a power cord 14. The power toothbrush 10 includes a drive system 16 which drives a brushhead assembly 18 in a desired manner to produce cleaning or other desired oral effect. The drive system 16 is typically powered by rechargeable batteries 17, which are charged by the charger 12 when the device is not in use. The drive system 16 is controlled by a microprocessor 22 which is programmed to control the operation of the drive system 16 to produce the desired brushhead movement. Such a general arrangement is well known in the art of power toothbrushes.

As indicated above, as electric toothbrushes have become more sophisticated, various features, typically in the form of what is referred to as different modes of operation, have been added to the usual toothbrush capability. The drive system 16 moves the brushhead differently for the different modes. Selection is achieved through a user interface 26. For instance, three different mode selections are visually represented/indicated on the user interface panel 26 in FIG. 1, with a first mode selection represented at 28 being for a normal vibration, a second mode selection represented at 30 being for a soft (gentle) vibration, typically with less amplitude and/or speed, than the first mode, and a third mode selection represented at 32 being for a massage mode, involving a different type (massage-like) of vibration. Other modes can be added as well. Three mode selections are provided just for illustration.

In addition, the various modes can be combined in various ways to produce multi-function modes, also referred to as routines, in which two or more modes are combined in one brushing event, each with predetermined times within the event. Typically, but not necessarily, each mode, and each multi-function mode or routine, will operate for the same overall time (the brushing event time), although the brushing event times for the various modes and routine can also be different, as pre-programmed, if desired. The mode/routine indications are represented as a group at 31.

In the present arrangement, toothbrush 10 is controlled by an ON/OFF switch 25 which is operated by the user to turn the toothbrush on and off. Turning the toothbrush on will initiate typically the pre-programmed time for a single brushing event, e.g. two minutes. Once the pre-programmed time has elapsed, the toothbrush automatically turns off. In the present arrangement, ON/OFF switch 25 is a pushbutton switch; different switches, however, can be used.

In addition, toothbrush 10 includes a mode select button 29 which can also be a pushbutton switch or similar switch member. In the embodiment shown, the mode select switch 29 controls the selection of particular modes and routines available in the toothbrush.

The mode select button 29 is operated to select a particular mode or routine available in the microprocessor prior to the application of power to the brushhead, i.e. when the ON/OFF switch is in an OFF condition. This is an important structural aspect of the arrangement. The microprocessor can receive instructions and change modes/routines without the brushhead moving.

Typically, prior to the initiation of brushhead motion, such as when the toothbrush is removed from the charger 14, the microprocessor of the toothbrush will be in its "normal" or "default" mode, in which it will control the drive system 16 to produce a normal brushhead action. This will involve a brushhead vibration having a preselected amplitude and frequency for normal cleansing of the teeth. One example of such a normal mode of vibration is an angle $\rho$ of motion of 11° at a frequency of approximately 262 Hz. It is not necessary, however, in the present invention, that the toothbrush return to its normal (default) mode upon or prior to the application of power to the brushhead, such as by placement of the toothbrush in the charger upon completion of a brushing event. It could, for instance, retain the operating mode of the last usage.

The toothbrush thus has three operating states. In a first state, the brushhead and the microprocessor are both "sleeping", i.e. off. In a second state, the mode button has been pushed so the modes are accessed by the microprocessor, but the toothbrush is not ON. In a third state, the brushhead is moving (the toothbrush is ON) in the mode selected.

Figure 2:
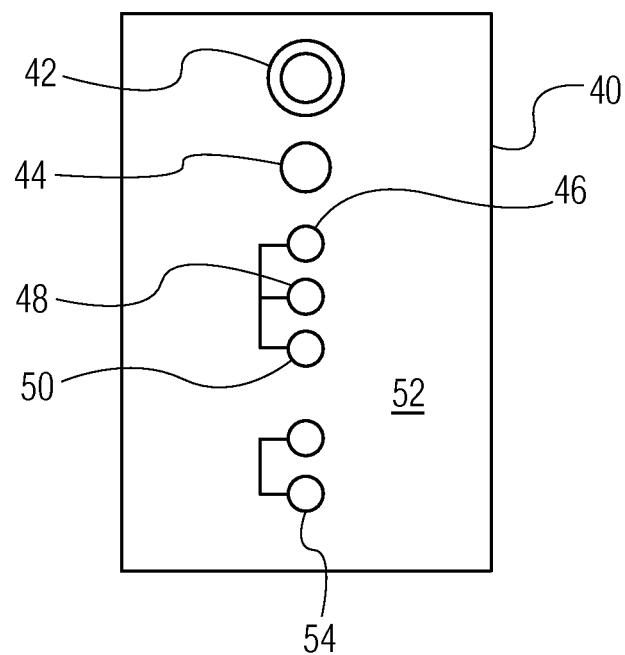
FIG. 2 is a more detailed view of the user interface assembly shown in FIG. 1.

Referring in particular now to FIG. 2, a visual indication of the operating mode status of the toothbrush is provided relative to a user interface 40. Again, a toothbrush could have three individual modes, each indicated with an LED lamp. An ON/OFF switch 42 and a mode switch 44 could also be lit with an LED. The three mode settings could be normal, shown at 46; gentle, which is characterized by less amplitude and perhaps a different frequency, at 44, and a massage-type vibration, effective for tissue stimulation, at 50. Two multi-mode functions, also referred to as routines, are shown at 52 and 54. For instance, for example only, routine 1, over a total event time of two minutes, could include 60 seconds of mode 1 action and 60 seconds of mode 2 action, while a second routine could be 60 seconds of mode 2 action and 60 seconds of mode 3 action. Each of the routines is programmed into the microprocessor 22, which controls the drive system 16 accordingly. It should be understood, however, that the routines set forth above are examples only and other routines can be programmed, as desired by the manufacturer.

The selection of the particular mode or routine desired is accomplished by simply successively pushing mode select button 44, when the brushhead 18 is not moving. The individual LED lights associated with the modes will be lit successively, as the mode button 44 is operated, to provide a clear visual indication of which mode/routine in the microprocessor has at that point been selected.

In addition, the interface arrangement includes a timer 56 (FIG. 1) which is initiated upon operation of the mode select button and provides a selected amount of time in which the ON/OFF switch must be operated from OFF to ON. If the ON/OFF switch is not operated within that time, the toothbrush reverts to its default condition, i.e. normal mode. In the embodiment shown, the time is 30 seconds, but this can be varied. Alternatively, the timer 56 may not be included, such that when the mode switch is operated to select a particular mode/routine, the toothbrush remains in that mode/routine until changed by the user. In operation, the LED light for the selected mode will remain on during the time that the toothbrush is actually operating in that mode.

In use, assuming a conventional arrangement in which the toothbrush is removed from the charger in a default or normal mode, the user will first press the mode select button 44, while the toothbrush is in an OFF condition. This will result in the "normal" LED 46 being lit. If the user desires another mode, or mode combination (routine), the mode select button is pushed successively, cycling through the mode/routine possibilities until the desired mode/routine is reached. The LED lights will come on successively during the selection process. When the desired mode is reached, the corresponding indicator light will be on, thereby confirming to the user that the microprocessor is now ready to control the drive system in the desired mode or routine.

At this stage of use, the device is out of the user's mouth and there is a clear indication to the user of the selected operational mode. No splattering of toothpaste or water is present because the device is not in an ON condition and the brushhead is thus not vibrating.

At this point, the toothbrush is placed in the mouth and the user will operate the ON/OFF button 42. Operation of the device then commences in the desired mode. The device will operate in that mode for the selected preprogrammed time, e.g. two minutes. At the end of that time, the toothbrush will shut off and typically, but not necessarily, the microprocessor will return to its "normal", i.e. default mode.

If the unit is switched OFF prior to the conventional two-minute timeout period, the elapsed time and the mode will be maintained for a selected period of time by another timer 27 within the toothbrush. Again, this could be 30 seconds, but could certainly be longer or even shorter if so desired.

Figure 3:
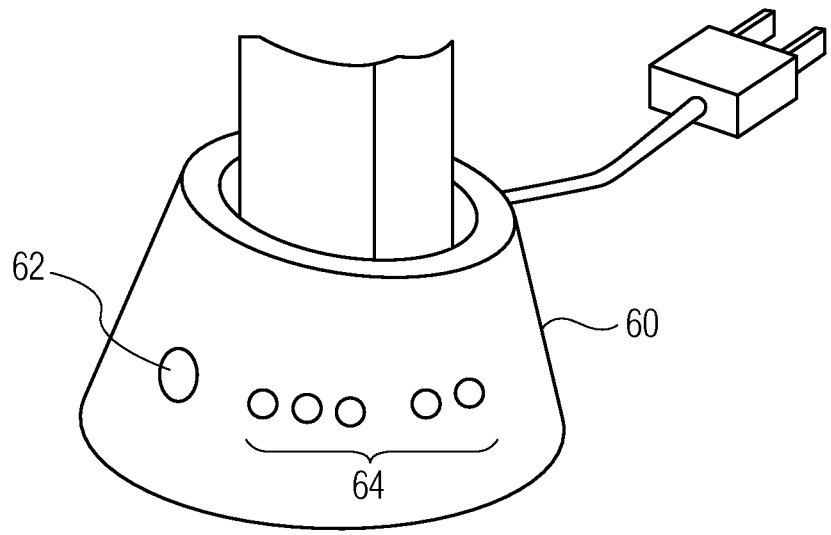
FIG. 3 is a schematic view of an alternate embodiment to that of FIGS. 1 and 2.

FIG. 3 shows an alternative mode display arrangement, located on the charger 60. The mode switch 62 and the various mode/routine indicators 64 are on the charger, communicating with the toothbrush via an RF or other communication link. Also, the mode switch could be on the toothbrush with the mode/routine indications being on the charger. The mode switch and indicators could also be on a completely separate unit.

With the above system, the user can select the desired mode or routine, confirm that the device is in that particular mode visually, and then proceed to operate the toothbrush without splattering. The LED indicating the selected mode will stay on, so that if the user wishes at any time to confirm the mode, they can simply push the ON/OFF button, remove the toothbrush from their mouth, and inspect the user interface to confirm the particular mode of operation.

Thus, a power toothbrush has been disclosed having a particular interface arrangement which permits a plurality of different operating modes, yet permits the user to select the mode and receive a visual indication thereof outside of the mouth, when the toothbrush is in an OFF condition, avoiding any splattering or other operating effect.

Although a preferred embodiment of the invention has been disclosed here for the purposes of illustration, it should be understood that various changes, modifications and substitutions may be incorporated in the embodiment without departing from the spirit of the invention, which is defined by the claims which follow.

What is claimed is:

1. A system for selection of operation of a power toothbrush operating at a sonic frequency, comprising:
a toothbrush assembly (10) having a first switch (25) operable by the user to control the ON/OFF condition of the toothbrush, and a second switch (29) separate from the first switch, operable by a user during the time that the first switch is in its OFF condition, to select one of a plurality of possible different modes of operation established in the toothbrush, wherein when the second switch is operated to select a particular mode of operation, the toothbrush will then operate in the particular mode when the first switch is thereafter operated to an ON condition; and
an indicator means (31) for indicating which mode has been selected, wherein the toothbrush assembly includes a microprocessor operating with a stored program for controlling at least three different modes, each mode having a different kind of brushhead vibration.

2. The system of claim 1, wherein said indicator means provides a visual indication of the selected mode.

3. The system of claim 2, wherein the visual indicator means is an LED.

4. The system of claim 2, wherein the selected visual indicator means stays on during the entire brushing event.

5. The system of claim 1, including a timer (56) which establishes a predetermined time during which the first switch must be operated following selection of a particular mode of operation by the user for the toothbrush to then operate in the particular mode, wherein when the first switch is not operated during said predetermined time, the toothbrush will default to a normal mode of operation, apart from a normal time of operation.

6. The system of claim 5, wherein the predetermined time is approximately 30 seconds.

7. The system of claim 1, wherein the first and second switches are located on a handle portion of the toothbrush.

8. The system of claim 7, wherein the indicator means is also located on the handle portion of the toothbrush.

9. The system of claim 1, wherein the second switch and the indicator means are located on a battery charger (12) for the power toothbrush, in which the power toothbrush is positioned when not in use.

10. The system of claim 1, wherein the toothbrush is programmed to revert to a normal mode of operation when the toothbrush turns off and is not turned back on within a preselected time.

11. The system of claim 1, wherein the stored program further includes two routines, each routine comprising at least two modes, each mode operating for a selected time during a single brushing event.

\* \* \* \* \*